(12) United States Patent
Wiegand et al.

(10) Patent No.: US 7,300,654 B2
(45) Date of Patent: *Nov. 27, 2007

(54) METHOD OF TREATING CORNEAL TRANSPLANT REJECTION IN HIGH RISK KERATOPLASTY PATIENTS

(75) Inventors: Stanley Wiegand, Croton on Hudon, NY (US); Jingtai Cao, Chappaqua, NY (US); Claus Cursiefen, Erlangen (DE)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 359 days.

This patent is subject to a terminal disclaimer.

(21) Appl. No.: 11/039,144

(22) Filed: Jan. 19, 2005

(65) Prior Publication Data

US 2005/0197291 A1    Sep. 8, 2005

Related U.S. Application Data

(63) Continuation-in-part of application No. 10/830,902, filed on Apr. 23, 2004.

(60) Provisional application No. 60/473,734, filed on May 28, 2003, provisional application No. 60/492,865, filed on Aug. 6, 2003.

(51) Int. Cl.
*A61K 38/18* (2006.01)
*C07K 14/71* (2006.01)
*C12N 15/62* (2006.01)

(52) U.S. Cl. .............. 424/134.1; 424/192.1; 514/2; 514/12; 530/350; 536/23.4

(58) Field of Classification Search ............ None
See application file for complete search history.

(56) References Cited

U.S. PATENT DOCUMENTS

2005/0004027 A1 * 1/2005 Wiegand et al. ............. 514/12
2006/0172944 A1 * 8/2006 Wiegand et al. ............. 514/12

OTHER PUBLICATIONS

Phillips, A.J. (2001). The challenge of gene therapy and DNA delivery. J. Pharm. Pharmacol. 53:1169-1174.*
Stagner et al. (2004). Beta-cell sparing in transplanted islets by vascular endothelial growth factor. Transplant. Proc. 36:1178-1180.*
Yi et al. (2007). VEGF gene therapy for the survival of transplanted fat tissue in nude mice. J. Plast. Reconstr. Aesthet. Surg. 60:272-278.*
Palù et al. (1999). In pursuit of new developments for gene therapy. J. Biotechnol. 68:1-13.*
de Freitas et al. (2006). Causes and risk factors for graft failure in surgeries performed by physicians in fellowship training. Cornea. 25(3):251-256.*
Yatoh, et al., TRANSPLANTATION, vol. 66, No. 11, pp. 1519-1524 (1998).

* cited by examiner

*Primary Examiner*—Christine J. Saoud
*Assistant Examiner*—Jon M Lockard
(74) *Attorney, Agent, or Firm*—Valeta Gregg, Esq.

(57) ABSTRACT

Methods of preventing, reducing, or treating corneal transplant rejection to improve transplant survival in a high risk subject comprising administering an agent capable of blocking or inhibiting vascular endothelial growth factor (VEGF) are provided. The methods are useful for inhibiting or preventing corneal transplant rejection in a human subject who is the recipient of a transplanted cornea.

4 Claims, No Drawings

METHOD OF TREATING CORNEAL TRANSPLANT REJECTION IN HIGH RISK KERATOPLASTY PATIENTS

CROSS-REFERENCE TO RELATED APPLICATIONS

This application is a continuation in part of U.S. Ser. No. 10/830,902 filed 23 Apr. 2004, which claims the benefit under 35 USC § 119(e) of U.S. Provisionals 60/473,734 filed 28 May 2003 and 60/492,865 filed 6 Aug. 2003, which applications are herein specifically incorporated by reference in their entirety.

BACKGROUND

1. Field of the Invention

The field of the invention is related to methods of using VEGF antagonists to reduce, prevent, or treat corneal transplant rejection, thus improving long-term transplant survival.

2. Description of Related Art

It has previously been reported that topical application of an anti-VEGF neutralizing antibody suppresses acute allograft rejection in a rat corneal transplant model (Yatoh et al. (1998) Transplantation 66(11):1519-24).

BRIEF SUMMARY OF THE INVENTION

The invention is based in part on the finding that administration of an agent capable of blocking or inhibiting vascular endothelial growth factor (VEGF) prevents corneal transplant rejection. The experiments, described below, conducted in an animal model of corneal transplantation show that long-term transplant survival is promoted by blocking VEGF-mediated activity.

In a first aspect, the invention features a method of improving transplant survival in a high-risk keratoplasty subject, comprising administering to the subject an agent capable of blocking, inhibiting, or ameliorating vascular endothelial growth factor (VEGF)-mediated activity, such that transplant survival is improved.

In specific embodiments, the agent capable of blocking, inhibiting, or ameliorating VEGF-mediated activity is a VEGF antagonist. The VEGF antagonist may be a polypeptide, an antibody, a small molecule, or a nucleic acid. More specifically, the VEGF antagonist includes a VEGF trap selected from the group consisting of acetylated Flt-1(1-3)-Fc, Flt-1(1-3$_{R->N}$)-Fc, Flt-1(1-3$_{\Delta B}$)-Fc, Flt-1(2-3$_{\Delta B}$)-Fc, Flt-1(2-3)-Fc, Flt-1D2-VEGFR3D3-Fc$\Delta$C1(a), Flt-1D2-Flk-1D3-Fc$\Delta$C1(a), and VEGFR1R2-Fc$\Delta$C1(a). In a specific and preferred embodiment, the VEGF trap is VEGFR1R2-Fc$\Delta$C1(a) (also termed VEGF trap$_{R1R2}$) having the nucleotide sequence set forth in SEQ ID NO: 1 and the amino acid sequence set forth in SEQ ID NO: 2. The invention encompasses the use of a VEGF trap that is at least 90%, 95%, 98%, or at least 99% homologous with the nucleotide sequence set forth in SEQ ID NO: 1 and/or the amino acid sequence set forth in SEQ ID NO:2.

Administration of the agent may be by any method known in the art, including intraocular, periocular, retrobalbar, intradermal, intramuscular, intraperitoneal, intravenous, subcutaneous, intranasal, oral, or topical routes of administration. Preferable, administration to the subject in need of the agent is topical administration to the eye or subconjunctival administration. Administration may occur prior to or following corneal transplantation, preferably following surgery. Administration may also include a second agent, such as an immunosuppressive agent.

The subject to be treated is preferably a human subject who has or will receive a corneal transplant and who is considered to be a high-risk keratoplasty subject. High-risk keratoplasty subjects include subjects suffering from any of the following conditions: corneal surface disease, systemic immunological disorder, neovascularization in the cornea, corneal injury, such as alkali burn injury, a previous corneal graft rejection, or having an ongoing ocular inflammation at the time of corneal grafting.

In a second aspect, the invention features a method of preventing corneal transplant rejection in a high-risk keratoplasty subject, comprising administering to the subject an agent capable of blocking, inhibiting, or ameliorating vascular endothelial growth factor (VEGF)-mediated activity, such that corneal transplant rejection is prevented.

In a third aspect, the invention features a method of reducing the incidence of corneal transplant rejection in a high-risk keratoplasty subject, comprising administering to the subject an agent capable of blocking, inhibiting, or ameliorating vascular endothelial growth factor (VEGF)-mediated activity, such that the incidence of corneal transplant rejection is reduced.

In a fourth related aspect, the invention features a method of treating corneal transplant rejection in a high-risk keratoplasty subject, comprising administering to the subject an agent capable of blocking, inhibiting, or ameliorating vascular endothelial growth factor (VEGF)-mediated activity, such that corneal transplant rejection is treated.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General Description

Experiments were undertaken to evaluate occurrence and time course of hem- and lymphangiogenesis after normal-risk corneal transplantation and to test whether pharmacologic strategies inhibiting both processes improve long-term graft survival. As described in the Experiment 1 of the experimental section below, normal-risk allogeneic (C57BL/6 to BALB/c) and syngeneic (BALB/c to BALB/c) corneal transplantations were performed and occurrence and time course of hem- and lymphangiogenesis after keratoplasty was observed using double immunofluorescence of corneal flatmounts (with CD31 as panendothelial and LYVE-1 as lymphatic vascular endothelial specific marker). A molecular trap designed to eliminate VEGF-A ("VEGF Trap$_{R1R2}$"; 12.5 mg/kg) was tested for its ability to inhibit both processes after keratoplasty and to promote long-term graft survival (intraperitoneal injections on the day of surgery and 3, 7, and 14 days later). The results show that no blood or lymph vessels were detectable immediately after normal-risk transplantation in either donor or host cornea, but hem- and lymphangiogenesis were clearly visible at day 3 after transplantation. Both vessel types reached donor tissue at one week after allo- and similarly after syngeneic grafting. Early postoperative trapping of VEGF-A significantly reduced both hem- and lymphangiogenesis and significantly improved long-term graft survival (78% versus 40%; $p<0.05$). There is concurrent, VEGF-A-dependent hem- and lymphangiogenesis after normal-risk keratoplasty within the preoperatively avascular recipient bed. Inhibition of hem- and lymphangiogenesis (which mediate the efferent and afferent arms of an immune response) after normal-risk corneal transplantation improves long-term graft survival, establishing that early postoperative hem- and lymphangiogenesis are risk factors for graft rejection even in normal-risk eyes.

Experiments were also undertaken to evaluate the effect of VEGF trap on the long-term graft survival after high-risk corneal transplantation. As describe in Experiment 2 below, high-risk allogeneic (C57BL/6 to BALB/c) corneal transplantations were performed and long-term graft outcome were measured. The results show that while all transplanted corneas were rejected at day 21, 31% of the corneas survived in mice received VEGF trap treatment (25 mg/kg/mouse, at 0, 4, 7, and 14 days) after the transplantation.

VEGF Antagonists

In one aspect of the invention, VEGF-mediated activity is blocked or inhibited by the use of VEGF receptor-based blockers of VEGF-mediated activity. A non-limiting example of a VEGF receptor-based blocker includes, but is not limited to, VEGFR1R2-FcΔC1(a). Other suitable receptor-based blockers include acetylated Flt-1(1-3)-Fc, Flt-1(1-3$_{R->N}$)-Fc, Flt-1(1-3$_{\Delta B}$)-Fc, Flt-1(2-3$_{\Delta B}$)-Fc, Flt-1(2-3)-Fc, Flt-1D2-VEGFR3D3-FcΔC1(a), Flt-1D2-Flk-1D3-FcΔC1(a). For a complete description of these and other VEGF-receptor-based blockers, including pegylated receptor-based blockers, see PCT Publication No. WO/00/75319, the contents of which is incorporated in its entirety herein by reference.

In addition to the VEGF receptor-based blockers described in PCT Publication No. WO/00/75319, variants and derivatives of such VEGF receptor-based blockers are also contemplated by the invention. The sequence of the variants or derivatives may differ by a change which is one or more additions, insertions, deletions and/or substitutions of one or more nucleotides of the sequence set forth in SEQ ID NO:1. Changes to a nucleotide sequence may result in an amino acid change at the protein level, or not, as determined by the genetic code. Thus, nucleic acid according to the present invention may include a sequence different from the sequence shown in SEQ ID NO:1, yet encode a polypeptide with the same amino acid sequence as SEQ ID NO: 2. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant or derivative of the sequence shown in SEQ ID NO:2 is further provided by the present invention. Nucleic acid encoding such a polypeptide may show at the nucleotide sequence and/or encoded amino acid level greater than about 90%, 95%, 98%, or 99% homology with the coding sequence shown in SEQ ID NO:1 and/or the amino acid sequence shown in SEQ ID NO:2. For amino acid "homology", this may be understood to be similarity (according to the established principles of amino acid similarity, e.g. as determined using the algorithm GAP (Genetics Computer Group, Madison, Wis.)) or identity. GAP uses the Needleman and Wunsch algorithm to align two complete sequences that maximizes the number of matches and minimizes the number of gaps. Generally, the default parameters are used, with a gap creation penalty=12 and gap extension penalty=4.

Individual components of the VEGF-specific fusion proteins of the invention may be constructed by molecular biological methods known to the art with the instructions provided by the instant specification. These components are selected from a first cellular receptor protein, such as, for example, VEGFR1; a second cellular receptor protein, such as, for example, VEGFR2; a multimerizing component, such as an Fc.

Specific embodiments of the VEGF-specific fusion proteins useful in the methods of the invention comprise a multimerizing component which allows the fusion proteins to associate, e.g., as multimers, preferably dimers. Preferably, the multimerizing component comprises an immunoglobulin-derived domain. Suitable multimerizing components are sequences encoding an immunoglobulin heavy chain hinge region (Takahashi et al. 1982 Cell 29:671-679); immunoglobulin gene sequences, and portions thereof.

The nucleic acid constructs encoding the fusion proteins useful in the methods of the invention are inserted into an expression vector by methods known to the art, wherein the nucleic acid molecule is operatively linked to an expression control sequence. Host-vector systems for the production of proteins comprising an expression vector introduced into a host cell suitable for expression of the protein are known in the art. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NSO cell.

Treatment Population

A suitable subject for treatment by the method of the invention is a human who is a high-risk keratoplasty subject and who has received or will receive a corneal transplant. Corneal transplantation is the oldest, most successful and most commonly performed tissue transplantation, with nearly 40,000 transplantations a year alone in the US. When corneal grafts are placed into an avascular recipient bed (so-called normal-risk keratoplasty), 2-year graft survival rates approach 90% under cover of topical steroids, even without HLA-matching. This very successful outcome is attributed to corneal immune privilege, i.e. the phenomenon of suppressed corneal inflammation induced by an array of endogenous mechanisms downregulating alloimmune and inflammatory responses in the cornea and its bed. These mechanisms include the lack of both afferent lymphatic and efferent blood vessels in the normal-risk recipient cornea, lack of MHC II$^+$ antigen presenting cells (APCs), FASL-expression on corneal epithelium and endothelium, and the anterior chamber associated immune privilege (ACAID) directed at graft antigens etc. (Streilein et al. (1999) Transplant Proc. 31:1472-1475).

In contrast, survival rates of cornea grafts placed into vascularized, not immune-privileged recipient beds (so called high-risk keratoplasty) drop significantly to below 50% (even with local and systemic immune suppression). Pre-existing corneal stromal blood vessels have been identified as strong risk factors for immune rejection after corneal transplantation, both in the clinical setting as well as in the well-defined mouse model of corneal transplantation (Sano et al. (1995) Invest. Ophthalmol. Vis. Sci. 36:2176-85). Recently, in addition to blood vessels, biomicroscopically undetectable lymphatic vessels have been found in association with blood vessels in vascularized high-risk human corneas (Cursiefen et al. (2003) Cornea. 22:273-81) and it is likely that corneal lymphatic vessels enable effective access of donor and host APCs and antigenic material to regional lymph nodes where accelerated sensitisation to graft antigens occurs (Liu et al. (2002) J. Exp. Med. 195: 259-68) even in the normal-risk setting (with a preoperatively avascular recipient bed), where mild corneal hemangiogenesis develops after keratoplasty. Outgrowth of new blood vessels from the limbal arcade towards the graft can be observed within the first postoperative year in about 50% of patients undergoing normal-risk keratoplasty, and in 10% of patients these new blood vessels even reach the interface or invade donor tissue (Cursiefen et al. (2001) Graefes Arch. clin. Exp. Ophthalmol. 39:514-21) at corneal suture sites, and then proceed centrally.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Various delivery systems are known and can be used to administer an active agent of the invention, e.g., delivery systems suitable for topical administration, preferably topical administration directly to the eye, or subconjunctival administration, as well as other delivery systems such as those that utilize encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction are preferably topical or subconjunctival, but may be enteral or parenteral including but are not limited to intraocular, periocular, retrobalbar, intradermal, intramuscular, intraperitoneal, intravenous, subcutaneous, intranasal, and oral routes. The active agents may be administered by any convenient route, for example by absorption through epithelial (e.g. topical administration to the eye) or mucocutaneous linings (e.g., oral mucosa, intestinal mucosa, etc.) or infusion or bolus injection, and may be administered together with other biologically active agents. Administration can be systemic or local. Administration can be acute or chronic (e.g. daily, weekly, monthly, etc.) or in combination or alteration with other agents. Pulmonary administration can also be employed, e.g., by use of an inhaler or nebulizer, and formulation with an aerosolizing agent.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by topical administration, subconjunctival or periocular administration, intraocular administration, local infusion during surgery, e.g., by injection, by means of a catheter, or by means of an implant, said implant being of a porous, non-porous, or gelatinous material, including membranes, such as sialastic membranes, fibers, or commercial skin substitutes.

Pharmaceutical Compositions

Pharmaceutical compositions useful in the practice of the method of the invention include a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous, subcutaneous, or intramuscular administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention that will be effective in the treatment or prevention of corneal transplant rejection can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 50-5000 micrograms of active compound per kilogram body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide levels that are sufficient to maintain therapeutic effect. One having skill in the art will be able to optimize therapeutically effective local dosages without undue experimentation.

Combination Therapies

In numerous embodiments, the VEGF blockers of the present invention may be administered in combination with one or more additional compounds or therapies or medical procedures. For example, suitable therapeutic agents for use in combination, either alternating or simultaneously, with the VEGF blockers may include topically administered immunosuppressive agents such as corticosteroids, dexamethasone, cyclosporin A, or anti-metabolic agents or systemically administered immunosuppressive agents such as corticosteroids, dexamethasone, cyclosporin A, FK506, or anti-metabolic agents, as well as other agents effective to treat, reduce, or prevent corneal transplant rejection (see Barker, N H, et al., (2000) Clin Exp Opthal 28:357-360). Other suitable therapeutic agents for use in combination, either alternating or simultaneously, with the VEGF blockers of the subject invention may include blockers that can block other VEGF family members such as VEGF-C and VEGF-D.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Inhibition of Corneal Lymphangiogenesis and Angiogenesis After Normal-Risk Keratoplasty Using VEGFR1R2-FcΔC1(a)

Mice and anesthesia. Six to 8 weeks old male C57BL/6 mice were used as donors and same-aged male BALB/c mice (Taconic, Germantown, N.Y.) as recipients in the mouse model of normal-risk keratoplasty (Sonoda et al. (1992) Transplantation 54:694-704). For syngeneic transplantations, 6-8 weeks old male BALB/c mice were used both as donors as well as recipients. For the dose response studies, 8 weeks old male C57BL/6 mice were used. All animals were treated in accordance with the ARVO Statement for the Use of Animals in Ophthalmic and Vision Research. Mice were anesthetized using a mixture of ketamine and xylazine (120 mg/kg body weight and 20 mg/kg body weight respectively).

Dose response of VEGF $Trap_{R1R2}$. Five different doses of VEGF-$Trap_{R1R\ 2}$ (SEQ ID NO:2) were tested in mice that received three interrupted intrastromal sutures (10-0 nylon, 50-µm-diameter, Sharpoint, Surgical Specialties Corporation, Reading; Pa.). Gentamicine and ophthalmic ointment were applied immediately after surgery. Following surgery (day 0), mice received a single subcutaneous injection of VEGF $Trap_{R1R2}$ (25 mg/kg, 12.5 mg/kg, 6.25 mg/kg, 2.5 mg/kg or 0.5 mg) or human Fc (12.5 mg/kg; control). Corneas were harvested on day 9 after suture placement, following an intravenous administration of an endothelial-specific fluorescein-conjugated lectin (*Lycopersicon esculentum*, Vector Laboratories, Burlingame, Calif.). The isolated corneas were flat-mounted on glass slides, and images of lectin-labeled vessels were captured using a Spot RT Digital camera (Diagnostic Instrument, Inc. Sterling Heights, Mich.) attached to a Nikon Microphot-FXA microscope (Nikon Inc. Garden City, N.Y.). Scion Image 1.62c (Scion Corporation, Frederick, Md.) was used to quantify the extent of corneal neovascularization.

Corneal transplantation in mice. Orthotopic corneal allografting in the mouse model of normal-risk keratoplasty was performed as described previously (Sonoda et al. (1992) supra). Donor corneas were excised by trephination using a 2.0 mm bore and cut with a curved vannas scissor. Until grafting, corneal tissue was placed in chilled phosphate-buffered saline. Recipients were anesthetized and the graft bed was prepared by trephining a 1.5 mm site in the central cornea of the right eye and discarding the excised cornea. The donor cornea was immediately applied to the bed and secured in place with 8 interrupted sutures (11-0 nylon, 70 µm diameter needles, Arosurgical, Newport Beach, Calif.). Antibiotic ointment (Oxymycin, Pharmafair, Hauppauge, N.Y.) was placed on the corneal surface and the eyelids sutured with 8-0 suture (Sharpoint, Reading, Pa.). Recipients of grafts in which bleeding developed in the immediate postoperative period were discarded from further evaluation. All grafted eyes were examined after 72 hours, and grafts with technical difficulties (hyphema, cataract, infection, loss of anterior chamber) were excluded from further consideration. Tarsorraphy and corneal sutures were removed after 7 days and grafts were then examined at least twice a week until week 8 post transplantation by slit-lamp microscopy and scored for opacity. The survival experiment was performed twice and comprised 10 and 12 mice per experiment in both groups, respectively. Clinical scores of corneal grafts for opacity were as follows: 0=clear; +1=minimal, superficial (nonstromal) opacity; pupil margin and iris vessels readily visible through the cornea; +2=minimal, deep (stroma) opacity; pupil margins and iris vessels visible; +3=moderate stromal opacity; only pupil margin visible; +4=intense stromal opacity; only a portion of pupil margin visible; +5=maximum stromal opacity; anterior chamber not visible. Grafts with opacity scores of +2 or greater after 2 weeks were considered to have been rejected. Syngeneic transplantations were performed and evaluated in a similar manner.

Immunohistochemistry and morphometry of angiogenesis and lymphangiogenesis in the cornea. Briefly, corneal flat mounts were rinsed in PBS, fixed in acetone, rinsed in PBS, blocked in 2% bovine serum albumin, stained with FITC-conjugated CD31/PECAM-1 overnight (Santa Cruz Biotechnology, Santa Cruz, Calif.; 1:100), washed, blocked, stained with LYVE-1 (1:500; a lymphatic endothelium specific hyaluronic acid receptor (Cursiefen et al. (2002) Invest. Ophthalmol. Vis. Sci. 43:2127-35) washed, blocked, and stained with Cy3 (1:100; Jackson ImunoResearch Laboratories, West Grove, Pa.) and analyzed using a Zeiss Axiophot microscope. Digital pictures of the flat mounts were taken using Spot Image Analysis system. Then the area covered by $CD31^{+++}/LYVE-1^-$ blood vessels and $CD31^+/LYVE-1^{+++}$ lymph vessels was measured morphometrically on these flat-mounts using NIH Image software. The total corneal area was outlined using the innermost vessel of the limbal arcade as the border. The total area of blood versus lymphatic neovascularization was then normalized to the total corneal area and the percentage of the cornea covered by each vessel type calculated.

Neutralization of VEGF-A using VEGF $Trap_{R1R2}$. The VEGF $trap_{R1R2}$ (Regeneron Pharmaceuticals Inc, Tarrytown, N.Y. (Holash et al. (2002) Proc. Natl. Acad. Sci. USA 99:11393-8, herein specifically incorporated by reference in its entirety) was used in the transplant survival experiment at a concentration of 12.5 mg/kg intraperitoneally (i.p.) at time of surgery (CHO hVEGFR1 [lg domain 2] R2 [lg domain 3]Fc), and 3, 7, and 14 days after surgery. Human Fc-fragment given i.p. at same concentration and times was used in the control mice (sCHO h Fc).

Statistical analysis. Statistical significance was analyzed by Mann-Whitney's test. Differences were considered significant at $P<0.05$. Each experiment was performed at least twice with similar results. Graphs were drawn using Graph Pad Prism, Version 3.02.

Results. Dose response of angiogenesis inhibition by VEGF $Trap_{R1R2}$. VEGF-$Trap_{R1R2}$ at doses of either 25 mg/kg or 12.5 mg/kg completely inhibited suture-induced inflammatory corneal neovascularization. In contrast, doses of 6.25 mg/kg and 2.5 mg/kg produced ~50% and ~20% inhibition of corneal neovascularization, respectively, while the lowest dose tested, 0.5 mg/kg, had a negligible effect (<5% inhibition). Therefore, for subsequent experiments a dose of 12.5 mg/kg VEGF $Trap_{R1R2}$ was chosen.

Rapid and parallel onset of hemangiogenesis and lymphangiogenesis after normal-risk allogeneic corneal transplantation. To determine whether the mild and temporary hemangiogenesis occurring after normal-risk keratoplasty is accompanied by lymphatic vessel outgrowth from the limbus into the normally alymphatic cornea, we studied the time course of ingrowth of both vessel types at days 0, 3, 7, 14, 21, and 28 after allogeneic keratoplasty (only accepted grafts). Immediately after surgery, blood and lymphatic vessels were not detectable either in the host or in donor tissue using biomicroscopy and immunohistochemistry on corneal flat mounts. But, at day 3 after allografting, both methods revealed new blood vessels growing into the cornea already ⅓ to halfway towards the graft interface. By day 7 these vessels had usually reached the donor tissue, but they rarely invaded the donor tissue itself. Analyzing flatmounts stained with LYVE-1 as a lymphatic vessel specific marker showed that $CD31^{+++}/LYVE-1^-$ blood vessels were regularly accompanied by $LYVE-1^{+++}/CD31^+$ lymphatic vessels. Both vessel types reached the interface simultaneously at day 7. Thereafter, coincident with suture removal, both vessel types started to regress (if no immune rejection occurred; data not shown).

No difference in postkeratoplasty hem- and lymphangiogenesis between syngeneic and allogeneic corneal transplantation. To determine whether the simultaneous induction of hem- and lymphangiogenesis after normal-risk keratoplasty is primarily an effect of the surgical trauma, suturing and wound healing processes or secondary to early immunological rejection reactions, we compared speed and extent of both hem- and lymphangiogenesis occurring after keratoplasty between allogeneic (C57BL/6 into BALB/c) and syngeneic grafts (BALB/c into BALB/c) at day 3, 7, 14, 21, 28 after transplantation. In both groups, blood and lymphatic vessels grew out after keratoplasty and by day 3 reached about ⅓ to ½ of the limbus-interface distance. At day 7 after syngeneic and allogeneic grafting both vessel types had reached the interface, before they started to regress thereafter. Furthermore, there was no significant difference in the hem- and lymphvascularized area, comparing syngeneic and allogeneic grafts at 3 days (allogeneic: hemvascularized area [HA] 25.2±4.1% and lymphvascularized area [LA] 22.2±9.4% versus syngeneic HA: 23±2.7% and LA 19.4±7.2%) and 7 days (allogeneic HA: 53.8±11.2% and LA: 37.9±6.2% versus syngeneic HA: 55.9±8.2% and LA: 38±22.7%) after surgery (n=8 mice per group per time point).

Neutralization of VEGF-A after normal-risk keratoplasty inhibits postoperative hemangiogenesis and lymphangiogenesis. Mice received either intraperitoneal injections of VEGF $Trap_{R1R2}$ (12.5 mg/kg) at surgery and 3 days later, or in the controls the Fc-protein in the same dosage. At day 3 and 7 after surgery, the extent of hem- and lymphangiogenesis was compared between these two groups (n=6 mice per group per time point). At day 3 and day 7 after surgery, the hemvascularized area was significantly smaller in trap-treated mice (day 3: 15.8±4.0%; day 7: 25.2±13.3%) compared to mice just receiving the Fc-fragment (day 3: 25.8±4.4%; day 7: 48.3±12.8%; p<0.0001). This was also true for the lymphvascularized area comparing Trap- (9.5±9.4%) and Fc-treated mice on day 3 (21.5±9.3%; p<0.0001). At day 7, the lymphvascularized area was smaller, but not significantly different in the Trap-group (28.7±20.3%) compared to the Fc-group (51.5±23.8%; p=0.06). In contrast to results obtained in corneal injury models neither hem- nor lymphangiogenesis were completely inhibited by the VEGF Trap$_{R1R2}$ following corneal transplantation. However, the number of lymphatic vessels reaching the graft-host interface (10.6±0.6 versus 1.3±1.5 vessels) and the number of hours where the interface was filled with draining lymphatic vessels were much larger in the Fc-treated compared to the Trap-treated group (3±2 versus 0.2±0.3 hours; not significant due to small sample size) at day 7. This might indicate that lymphavascularized area per se is less decisive for host sensitisation than the contact area with donor tissue.

Partial inhibition of early postoperative hem- and lymphangiogenesis by trapping VEGF-A after normal-risk surgery improves long-term graft survival.

Since hem- and lymphangiogenesis occurring after normal-risk keratoplasty peaked around day 7, and regressed thereafter, and since both vascular processes could be significantly inhibited by early postoperative neutralization of VEGF-A, we determined whether inhibition of postkeratoplasty hem- and lymphangiogenesis during this interval improves graft survival. The long-term survival of C57BL/6 grafts placed into avascular BALB/c recipient beds was compared between mice receiving an i.p. injection of 12.5 mg/kg VEGF Trap$_{R1R2}$, or Fc-fragment alone, at surgery and 3, 7, and 14 days later. Trapping of VEGF-A postoperatively caused a significantly improved long-term graft survival at 8 weeks (78%), compared to grafts in eyes of Fc-treated controls (40%; p=0.044; n=22 in both groups).

Example 2

Inhibition of Corneal Lymphangiogenesis and Angiogenesis After High-Risk Keratoplasty Using VEGFR1R2-FcΔC1(a) Improves Corneal Graft Survival Three interrupted 11-0 sutures were placed into the corneal stroma of 23 female BALBc mice for 6 weeks when the corneas were intensely vascularized. Sutures were removed. Three weeks later, penetrating keratoplasty was performed with same-aged female C57BL/6 donors in the mouse model of corneal transplantation. The mice received transplants were then placed in two groups: thirteen mice in the treatment group and ten mice in the control group. Each mouse in the treatment group received 25 mg/kg VEGF Trap$_{R1R2}$ intraperitoneally at the day of surgery as well as 4, 7, and 14 days later; Each mouse in the control group received an equal amount of Fc-protein intraperitoneally at the day of surgery as well as 4, 7, and 14 days after the surgery. Postoperative survival of the grafts was analyzed for 8 weeks using a slit-lamp and Kaplan-Meier survival curves. Survival proportions at day 14 were 10% in the control group and 46% in the treatment group. At day 21 all ten control corneas were already rejected whereas 31% of the treated corneas remained un-rejected. After 8 weeks, all control corneas remained rejected, whereas 23% (3 out of 13) of the treated corneas were still un-rejected (p<0.05). Therefore, inhibition of hem- and lymphangiogenesis after high-risk keratoplasty improves corneal graft survival establishing postkeratoplasty neovascularization as a risk factor for immune rejections even in prevascularized high-risk eyes. Furthermore, modulation of surgery-related hem- and lymphangiogenesis after keratoplasty can significantly improve graft outcome.

The present invention may be embodied in other specific forms without departing from the spirit or essential attributes thereof.

We claim:

1. A method of improving transplant survival in a high risk keratoplasty subject, comprising administering to the subject prior to or following corneal transplantation, a first agent capable of blocking, inhibiting, or ameliorating vascular endothelial growth factor (VEGF)-mediated activity, such that transplant survival is improved, wherein the first agent is a VEGF-specific protein comprising VEGFR1R2-FcΔC1(a), and wherein the high risk subject suffers from a vascularized recipient bed.

2. The method of claim 1, wherein administration is intraocular, periocular, retrobalbar, intramuscular, intravenous, subcutaneous, subconjunctival, or topical.

3. The method of claim 1, further comprising administering a second agent to the subject, wherein the second agent is an immunosuppressive agent.

4. A method of reducing the incidence of corneal transplant rejection in a high risk subject, comprising administering to the subject prior to or following corneal transplantation, an agent capable of blocking, inhibiting, or ameliorating vascular endothelial growth factor (VEGF)-mediated activity, such that corneal transplant rejection is reduced, wherein the agent is a VEGF-specific protein comprising VEGFR1R2-FcΔC1(a), and wherein the high risk subject suffers from a vascularized recipient bed.

* * * * *

SEQUENCE LISTING

```
<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata agaaacttgt aaaccgagac     540
```

-continued

```
ctaaaaaccc agtctgggag tgagatgaag aaattttga gcaccttaac tatagatggt      600
gtaacccgga gtgaccaagg attgtacacc tgtgcagcat ccagtgggct gatgaccaag      660
aagaacagca catttgtcag ggtccatgaa aaggacaaaa ctcacacatg cccaccgtgc      720
ccagcacctg aactcctggg gggaccgtca gtcttcctct ccccccaaa acccaaggac      780
accctcatga tctcccggac ccctgaggtc acatgcgtgg tggtggacgt gagccacgaa      840
gaccctgagg tcaagttcaa ctggtacgtg acggcgtgg aggtgcataa tgccaagaca      900
aagccgcggg aggagcagta acagcacg taccgtgtgg tcagcgtcct caccgtcctg      960
caccaggact ggctgaatgg caaggagtac aagtgcaagg tctccaacaa agccctccca     1020
gcccccatcg agaaaaccat ctccaaagcc aaagggcagc cccgagaacc acaggtgtac     1080
accctgcccc catcccggga tgagctgacc aagaaccagg tcagcctgac ctgcctggtc     1140
aaaggcttct atcccagcga catcgccgtg gagtgggaga gcaatgggca gccggagaac     1200
aactacaaga ccacgcctcc cgtgctggac tccgacggct ccttcttcct ctacagcaag     1260
ctcaccgtgg acaagagcag gtggcagcag gggaacgtct tctcatgctc cgtgatgcat     1320
gaggctctgc acaaccacta cacgcagaag agcctctccc tgtctccggg taaatga       1377
```

<210> SEQ ID NO 2
<211> LENGTH: 458
<212> TYPE: PRT
<213> ORGANISM: homo sapiens

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
```

-continued

```
            225                 230                 235                 240
Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
                275                 280                 285

Tyr Val Asp Gly Val Glu Val His Asn Ala Lys Thr Lys Pro Arg Glu
                290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
                355                 360                 365

Leu Thr Lys Asn Gln Val Ser Leu Thr Cys Leu Val Lys Gly Phe Tyr
                370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys
450                 455
```